(12) United States Patent
Weber et al.

(10) Patent No.: US 7,887,497 B2
(45) Date of Patent: Feb. 15, 2011

(54) NON-IMMOBILIZING THUMB BRACE

(75) Inventors: James J. Weber, Santa Barbara, CA (US); David Auerbach, Calabasas, CA (US); Shane M. Woods, Fillmore, CA (US)

(73) Assignee: Weber Orthopedic Inc., Santa Paula, CA (US)

(*) Notice: Subject to any disclaimer, the term of this patent is extended or adjusted under 35 U.S.C. 154(b) by 278 days.

(21) Appl. No.: 12/077,154

(22) Filed: Mar. 18, 2008

(65) Prior Publication Data

US 2009/0240182 A1 Sep. 24, 2009

(51) Int. Cl.
*A61F 5/00* (2006.01)
*A61F 5/37* (2006.01)
*A41D 13/08* (2006.01)

(52) U.S. Cl. .................. 602/21; 602/20; 602/22; 602/23; 602/75; 602/62; 128/878; 128/879; 128/880; 2/16

(58) Field of Classification Search ............ 602/21, 602/22, 26, 1, 5, 20, 23, 62, 75; 2/6, 21, 2/22, 455, 16; 128/869, 878, 879, 880, 892
See application file for complete search history.

(56) References Cited

U.S. PATENT DOCUMENTS

| | | | |
|---|---|---|---|
| 4,441,490 A | * | 4/1984 | Nirschl ................. 602/21 |
| 4,584,993 A | | 4/1986 | Nelson |
| 4,658,441 A | | 4/1987 | Smith |
| 4,953,568 A | | 9/1990 | Theisler |
| 5,350,418 A | | 9/1994 | Janevski et al. |
| 5,356,371 A | | 10/1994 | Hubbard |
| D373,639 S | | 9/1996 | McKie |
| 5,682,611 A | | 11/1997 | Kline |
| 5,787,896 A | | 8/1998 | Sackett |
| 5,899,870 A | * | 5/1999 | Deirmendjian et al. ........ 602/21 |
| 6,101,628 A | | 8/2000 | Eearl |
| D473,653 S | | 4/2003 | Weaver, II |
| 6,702,772 B1 | * | 3/2004 | Colditz ................. 602/22 |

* cited by examiner

*Primary Examiner*—Patricia M Bianco
*Assistant Examiner*—Ophelia Hawthorne
(74) *Attorney, Agent, or Firm*—William W. Haefliger

(57) ABSTRACT

A unitary flexible body having an anchor portion wrapping about the wrist to secure the body there, the anchor portion freely offset from the thumb, palm and dorsum of the hand, the body having a support extension extending distally from the anchor portion in supporting relation with the Thenar Emminence of the palm, and extending part way about the thumb via the web space between the thumb and forefinger, and having terminal attachment to said anchor portion.

15 Claims, 5 Drawing Sheets

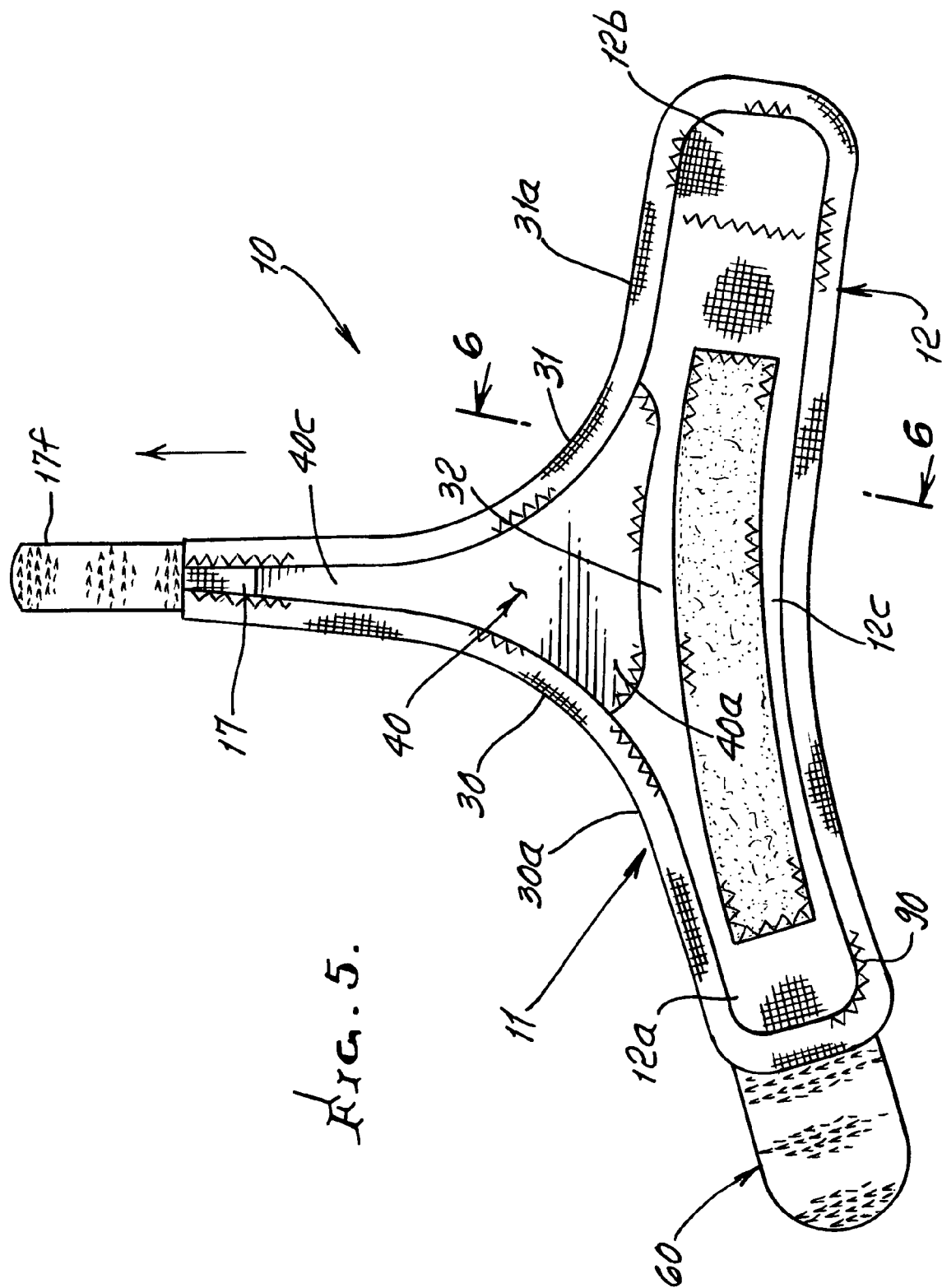

NON-IMMOBILIZING THUMB BRACE

BACKGROUND OF THE INVENTION

This invention relates generally to secure supporting of the CMC joint while allowing uninhibited motion of the thumb, in a selected position.

There is need for simple, effective, easily applied bracing of the CMC joint, while allowing uninhibited motion of the thumb, and particularly in accordance with the unusual advantages in structure, functions, and results as are now provided by the present invention.

SUMMARY OF THE INVENTION

It is a major object of the present invention to provide method and apparatus meeting the above need. Basically, the CMC support apparatus comprises a) a unitary flexible body having an anchor portion wrapping about the wrist to secure the body thereto, the anchor portion freely offset from the thumb, palm and dorsum of the hand, b) the body having a support extension extending distally from the anchor portion in supporting relation with the Thenar Emminence of the palm, and extending part way about the thumb via the web space between the thumb and forefinger, and having terminal attachment to said anchor portion.

Typically, the support extension has a distal portion releasably attached to the anchor portion of the body, and so as to exert web lifting force to the extension, while leaving the thumb free to flex. Also, the extension typically has connection to another anchor portion to extend adjacent the palm of the hand, and so as to effect pressure exertion by the apparatus against the CMC region.

Another object is to configure the support in extended position to have generally T-shaped flap configuration, the stem of the T-shape defining the support extension. That T-shape includes a cross-piece having edges which merge respectively with opposed edges of the extension, such merging edges defining two concave edge regions at said opposed edges of the extension.

A further object is to additionally provide a flat substantially non-stretchable reinforcement liner extending adjacent a flat side of the support extension to engage the web portion of the user's hand. The provided liner materially assists in creation and maintenance of pressure against the CMC joint area, and push-up pressure against the web zone between the thumb base and forefinger, at the palm side of the hand, contributing to non-immobilizing support of the thumb. Accordingly, the provided support comprises:

A') a unitary body consisting of an anchor wrapping around the wrist, to secure the anchor about the wrist so as to be substantially free of the thumb, palm and dorsum of the hand to allow for unrestricted motion of the thumb; and B') a support extension of the anchor, extending distally from the anchor for supporting the Thenar Emminence of the palm, and at least partially encircling the thumb by the way of the web space between the thumb and forefinger.

Also, securement is provided for the thumb position, and/or the CMC joint position, as for example during arthritis and/or sprain treatment, thereby to achieve maximum bracing comfort during such treatment.

These and other objects and advantages of the invention, as well as the details of an illustrative embodiment, will be more fully understood from the following specification and drawings, in which:

DRAWING DESCRIPTION

FIG. 5 is a view of the extended, T-shape of the apparatus, viewed toward its inner side to show an anchoring liner positioned and providing a sub-extension for co-operation with the main support extension to resist stretching of the main extension when tensioned as in FIGS. 1 and 2.

DETAILED DESCRIPTION

Figure 1:
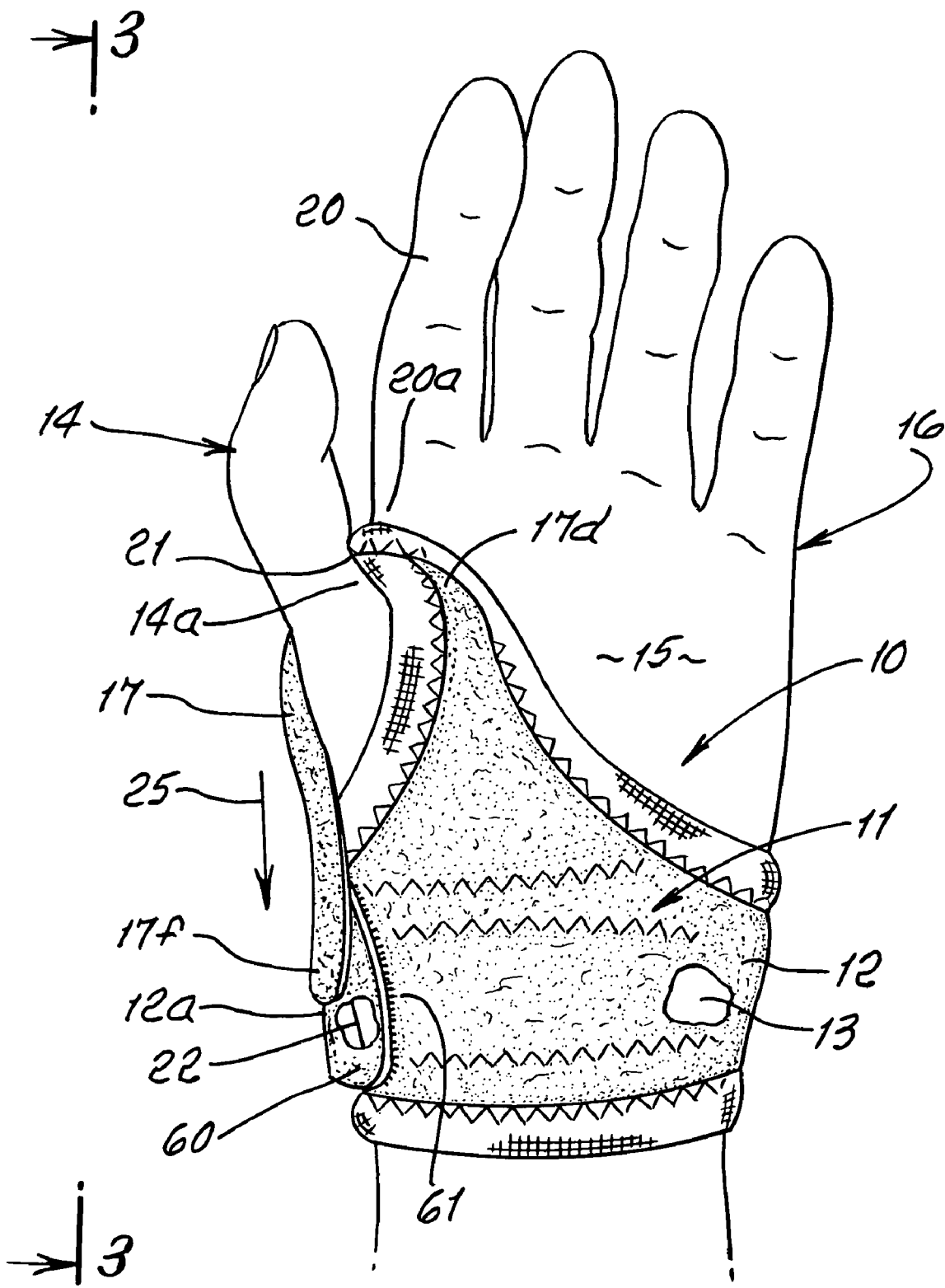
FIG. 1 is an upright hand palm side elevation view of the apparatus of the invention, in thumb and CMC joint supporting position.

In the preferred embodiment, as seen in the drawings, the CMC support 10 comprises a unitary flexible wrap-type body 11 having an anchor portion 12 with wings 12a and 12b (see FIG. 5) wrapping about the user's wrist 13 to secure the body in place, in wrapped and stretched condition, and with the wings freely offset from the thumb 14, the palm 15 and the dorsum of the hand 16. The body typically consists of flexible, resiliently stretchable, wrap material.

Figure 2:
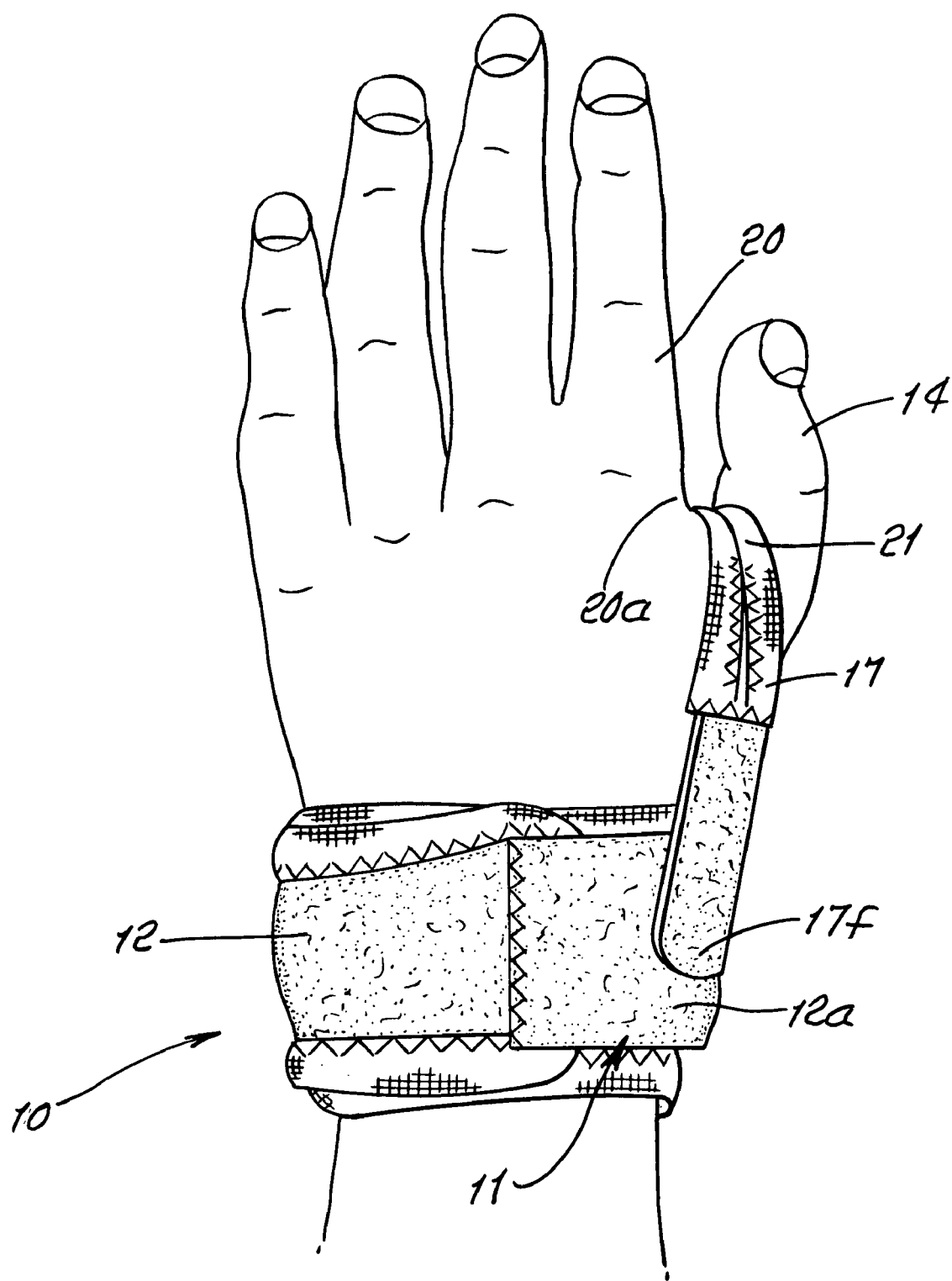
FIG. 2 is a rear side elevation view of the apparatus, anchored to the hand; and supporting the thumb in non-immobilizing mode.
Figure 3:
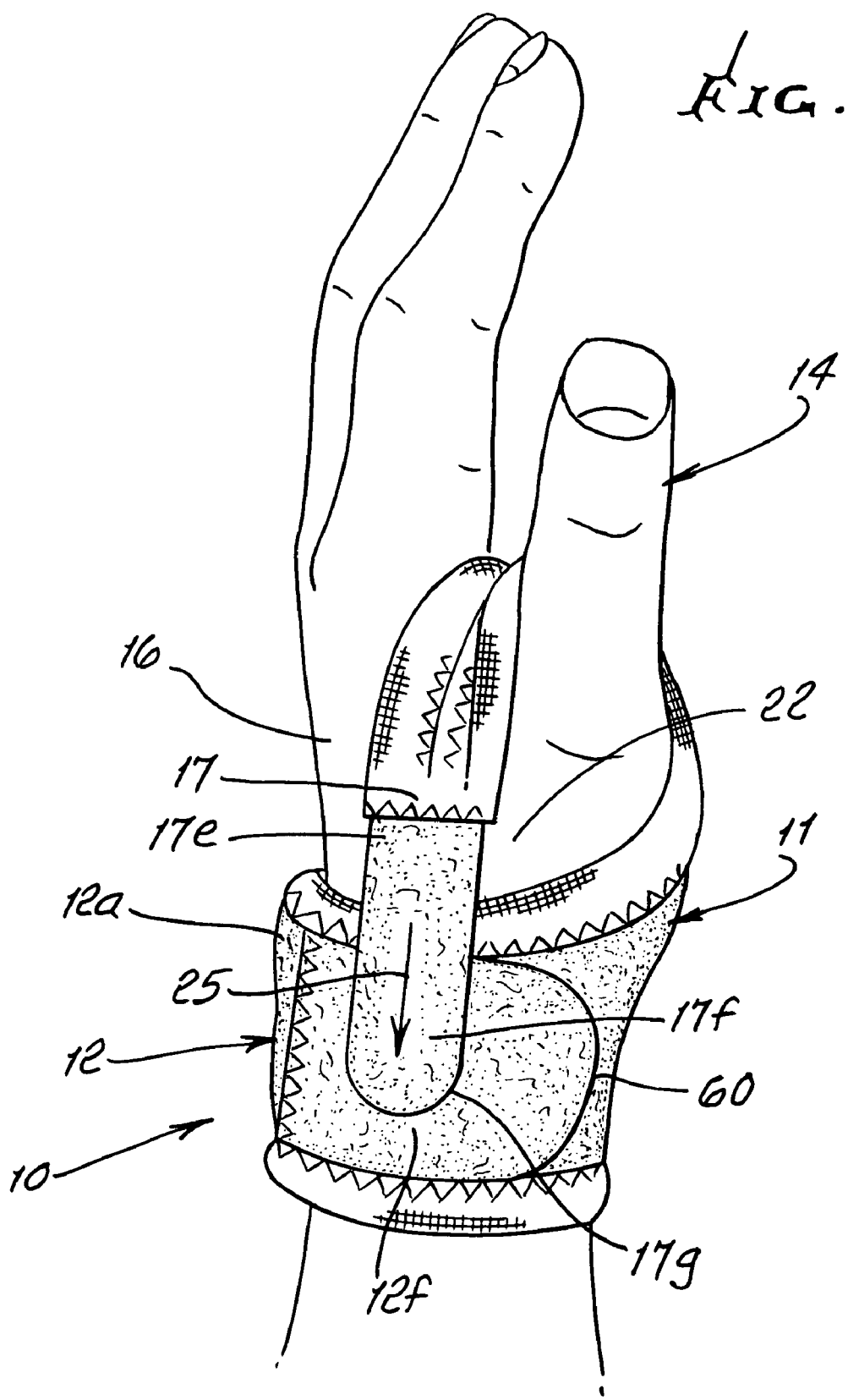
FIG. 3 is an elevation view taken on lines 3-3 of FIG. 1.
Figure 4:
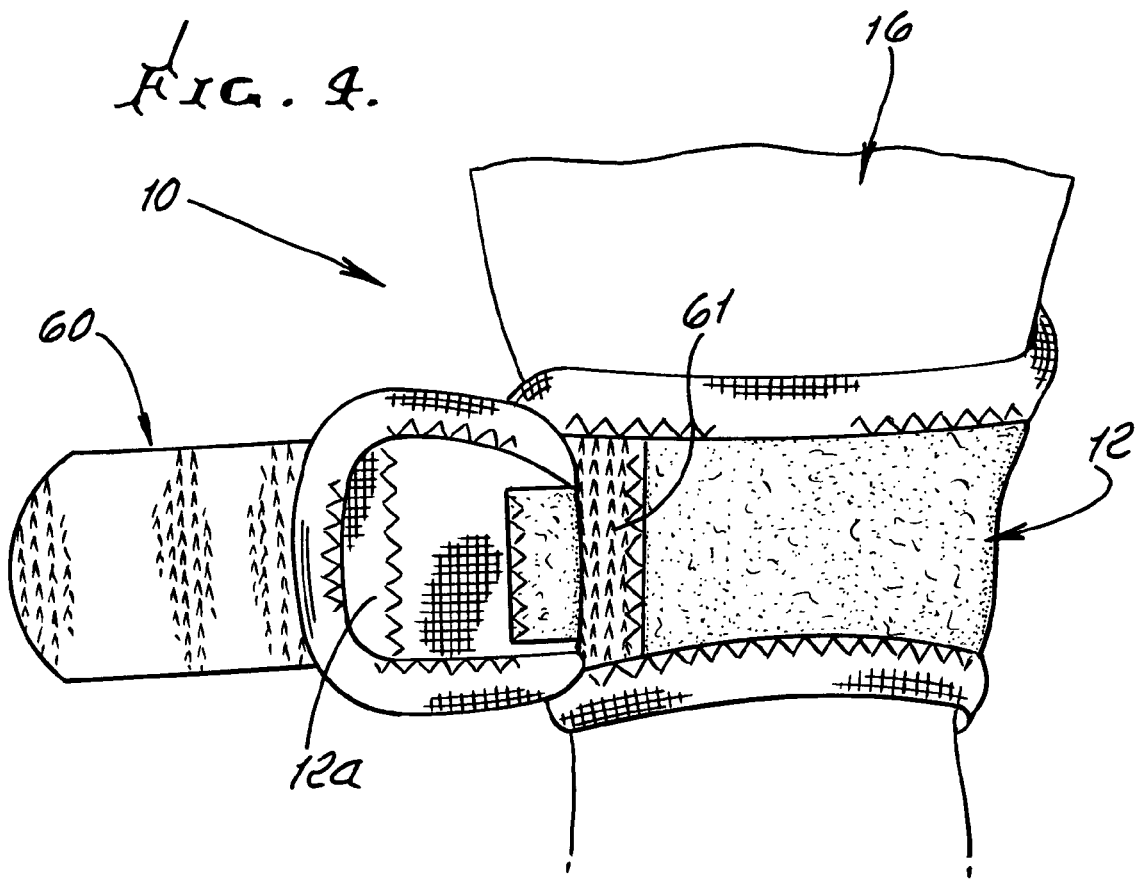
FIG. 4 is a view like FIG. 1, but showing the anchoring flap structure partly released.

The body includes a support extension 17, narrowed in width relative to the widths of the wings 12a and 12b, and extending distally away from the mid-region 12c of the anchor portion, and in supporting relation with the Thenar Emminence of the palm. The tapered extent 17d, of the support extension extends part way about the lower thumb, and via the web space or region 21 between lowermost extents 14a and 20a the thumb 14 and forefinger 20; also the strap is shown in FIGS. 1-3 as having terminal attachment at 17f to the body anchor portion 12, as shown by the support extension terminal press-on attachment to the body flap 12a spaced at the level of the CMC joint 22. See FIG. 3, which also shows extension wider portion 17e exerting pressure on the CMC joint region 22. Press-on attachment is typically provided by engagement of hook and loop surfaces at 12f and 17g, after tensioning of the strap downwardly (see arrow 25 in FIG. 3).

It will be understood that the support extension configuration, relative positioning as in FIGS. 1-6, and tensioning as referred to, combine to contribute to effective stabilizing pressurization of the CMC joint, without restricting thumb mobility (including flexing) and upward (i.e. lifting) stabilizing and comfortable pressurization of the web region 21 between the forefinger and thumb lowermost extent. In this regard, note in FIG. 5, the support extension upwardly tapering (in width) at concave edge regions 30 and 31, which merge at 30a and 31a with the upper edges of the body wings 12a and 12b. The support extension base enhanced width at 32 tapering upwardly between concave regions 30 and 31 in FIG. 5 provides enhanced yieldable resistance to support extension pull stretching at 25 during attachment, which enhances stabilizing force transmission to the CMC joint region in face-to-face proximity to 32. Such force transmission smoothly emanates in stabilizing manner from the body wings, due to the concave edge merging configurations at 30*a* and 31*a*.

Figure 6:
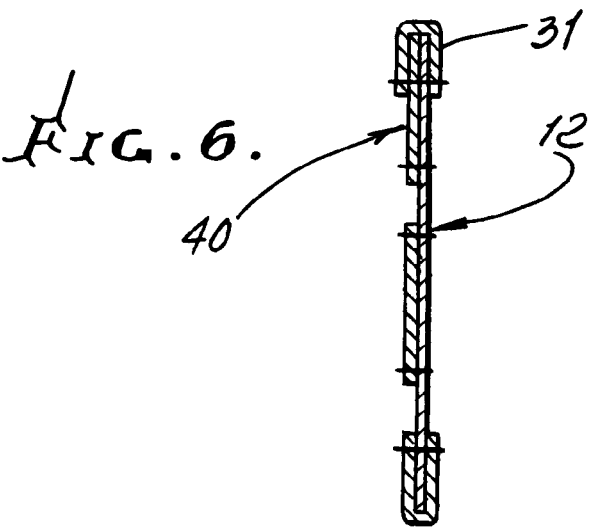
FIG. 6 is a section taken on lines 6-6 of FIG. 5.

Further contributing to the thumb stabilizing but non-immobilizing effects is a substantially non-stretchable, flexible, thin liner 40 shown in FIGS. 5 and 6 acting as a separator. It also has Y-shaped configuration with wings 40*a* and 40*b*, and tapered stem 40*c*, and typically edge stitched in place as shown at the inner side of body 12, to overlie the web region 21 and to push relatively upwardly on that region at the hand palm side, without discomforting the highly flexible skin of the user's hand, at that region. Upward push with separating affect contribute to stabilizing face-to-face force transmission to the CMC joint. Liner 40 may consist of a thin layer of leather or equivalent material to comfortably engage and push against web region 21. Note also in FIG. 5 that all or nearly all edges of the body 11 are fold-over seamed, and stitched as at 90. The liner is stitched to the extension 17, at its inner side.

FIGS. 1-3 show the body wings in anchor-wrapped condition, and held in place by hook and pile attachment of a tab 60 to body surface 61. See also FIG. 4 in this regard.

Accordingly, the basic method of the invention for supporting the CMC joint, includes the steps:

A. providing a unitary wrap body consisting of an anchor portion wrapping around the wrist, to secure the anchor portion about the wrist, sufficiently free of the thumb, palm and dorsum of the hand to allow for unrestricted motion of the thumb, and B. providing an extension of the anchor portion in the form of a tapered support extension extending distally away from the anchor portion and supporting the Thenar Emminence of the palm at least partially and encircling the thumb by way of the web space, and extending proximally away from the fingers with an extension free end attaching to the anchor.

Additional features and advantages include the face that the device does not cover the thumb, as a sleeve would; it leaves the thumb free to flex at the metacarpal joint while the CMC joint is pressurized; pressure applied at the web space between the thumb and forefinger, while the CMC joint is pressurized, puts the thumb into abduction while the CMC joint is stabilized.

It will be understood that a pinch effect is created between the support extension at said web region and the anchor portion, whereby pressure is created and exerted against the CMC joint region of the hand, when the device is attached in the positions shown in FIGS. 1-3.

We claim:

1. A CMC support, comprising
a) a unitary flexible support body having an anchor portion wrapping about the wrist to secure the body thereto, the anchor portion freely offset from the thumb, palm and dorsum of the hand,
b) the body having a support extension extending distally from the anchor portion in supporting relation with the Thenar Emminence of the palm, and extending part way about the thumb via the web space between the thumb and forefinger, and having terminal attachment to said anchor portion,
c) the support body in extended and flattened condition having flat generally T-shaped flap configuration, the T-shape defining a laterally extending cross-piece and a stem which tapers away from the central region of the cross-piece and a terminal in alignment with the stem, the stem and terminal extending longitudinally away from the cross-piece, the stem having laterally opposite edges which diverge toward the cross-piece and which merge arcuately with diverging edges of the cross-piece.

2. The support of claim 1 wherein said edges of the cross-piece defining define two like concave edge regions at said opposed edges of the support extension.

3. The support of claim 2 wherein said opposed edges of the support extension are defined by seam binding structure.

4. The support of claim 2 wherein a flat, substantially non-stretchable reinforcement liner extends adjacent a flat side of the support extension to engage said web portion of the user's hand.

5. The support of claim 1 including hook and loop material on the body to secure said anchor portion, and to secure the extension strap terminal to the anchor portion.

6. The support of claim 1 wherein
i) the body is stretchable
or ii) or the body is non-stretchable.

7. A CMC support, comprising
a) a brace configured for wrapping application of an anchor portion to the wrist of the user,
b) the brace including a support extension extensible over the web between the user's thumb and forefinger and so as to bear against the CMC joint portion of the user's hand,
c) the support extension having a distal portion releasably attachable to said anchor portion of the brace, and so as to exert web lifting force to the strap, while leaving the thumb free to flex,
d) the brace in extended and flattened condition having flat generally T-shaped flap configuration, the T-shape defining a laterally extending cross-piece and a stem which tapers away from the central region of the cross-piece and a terminal in alignment with the stem, the stem and terminal extending longitudinally away from the cross-piece, the stem having laterally opposite edges which diverge toward the cross-piece and which merge arcuately with diverging edges of the cross-piece.

8. The support of claim 7 wherein said edges of the cross-piece define two concave edge regions at said opposed edges of the support extension.

9. The support of claim 8 wherein said opposed edges of the support extension are defined by seam binding structure.

10. The support of claim 8 including a flat, substantially non-stretchable reinforcement liner extending adjacent a flat side of the support extension to engage said web portion of the user's hand.

11. The support of claim 7 wherein the support extension has connection to said anchor portion to extend adjacent the palm of the hand.

12. The method of providing for hand CMC support, which includes:
a) providing a unitary flexible support body having an anchor portion wrapping about the wrist to secure the body thereto, the anchor portion freely offset from the thumb, palm and dorsum of the hand,
b) the body provided to have a support extension extending distally from the anchor portion in supporting relation with the Thenar Emminence of the palm, and extending part way about the thumb via the web space between the thumb and forefinger, and having terminal attachment to said anchor portion,
c) the support body provided to have in extended and flattened condition a flat generally T-shaped flap configuration, the T-shape defining a laterally extending cross-piece, and a stem which tapers away from the central region of the cross-piece, and a terminal in alignment with the stem, the stem and terminal extending longitudinally away from the cross-piece, the stem having laterally opposite edges which diverge toward the cross-piece and which merge arcuately with diverging edges of the cross-piece.

13. The method of claim 12 including exerting lifting pressure on a hand region of said body that is defined by a web region of said extension.

14. The method which includes
   i) providing the CMC support of claim 1, and
   ii) attaching said CMC support to the hand to create a pinch effect between the support extension at said web space, and said anchor portion.

15. The method which includes
   i) providing a flexible brace anchor portion and a support extension from said anchor portion
   ii) and attaching said brace anchor portion to the wrist and said support extension over the web region between the thumb and forefinger with tension, thereby to create a pinch effect acting to create brace pressure exertion against the CMC joint region of the hand,
   iii) said anchor portion and extension provided to have in extended and flattened condition a flat generally T-shaped flap configuration, the T-shape defining a laterally extending cross-piece and a stem which tapers away from the central region of the cross-piece and a terminal in alignment with the stem, the stem and terminal extending longitudinally away from the cross-piece, the stem having laterally opposite edges which diverge toward the cross-piece and which merge arcuately with diverging edges of the cross-piece.

* * * * *